United States Patent
Moussa et al.

(10) Patent No.: US 10,743,590 B2
(45) Date of Patent: Aug. 18, 2020

(54) ISOLATOR SLEEVE SYSTEMS

(71) Applicant: CLEAN AIR ESSENTIALS 797 INC., Montreal (CA)

(72) Inventors: Magdi Moussa, Montreal (CA); Daniel Zini, Montreal (CA)

(73) Assignee: CLEAN AIR ESSENTIALS 797 INC., Montreal (CA)

( * ) Notice: Subject to any disclaimer, the term of this patent is extended or adjusted under 35 U.S.C. 154(b) by 0 days.

(21) Appl. No.: 15/576,790

(22) PCT Filed: Nov. 25, 2016

(86) PCT No.: PCT/CA2016/051387
§ 371 (c)(1),
(2) Date: Nov. 24, 2017

(87) PCT Pub. No.: WO2017/091890
PCT Pub. Date: Jun. 8, 2017

(65) Prior Publication Data
US 2018/0303170 A1    Oct. 25, 2018

Related U.S. Application Data

(60) Provisional application No. 62/261,411, filed on Dec. 1, 2015.

(51) Int. Cl.
*A61B 42/00* (2016.01)
*A41B 7/12* (2006.01)
(Continued)

(52) U.S. Cl.
CPC ............... *A41B 7/12* (2013.01); *A61B 42/00* (2016.02); *A61B 42/50* (2016.02); *B25J 21/02* (2013.01); *G21F 7/053* (2013.01); *A61G 10/005* (2013.01)

(58) Field of Classification Search
CPC ...... A61B 42/00; A61B 42/50; A61G 10/005; B25J 21/02; G21F 7/053
See application file for complete search history.

(56) References Cited

U.S. PATENT DOCUMENTS 3,140,495 A   7/1964   Gottwik
3,700,135 A   10/1972  Collier
(Continued)

FOREIGN PATENT DOCUMENTS

CA   2084917 A1   6/1993
EP   0411794 A1   2/1991
(Continued)

OTHER PUBLICATIONS

English abstract of EP0549450 A1 retrieved from Espacenet on Nov. 8, 2017.
(Continued)

*Primary Examiner* — Christine H Matthews
(74) *Attorney, Agent, or Firm* — BCF LLP (57) ABSTRACT

A cuff attachment for an isolator sleeve cuff, the cuff attachment comprising an annular band of substantially elastomeric material having an open first end and an open second end, the first end having a diameter which is wider than a diameter of the second end, the first end being adapted to be attachable to an isolator sleeve cuff, and the second end being adapted to releasably retain a plug therein. A plug for sealing the second end of the cuff attachment, the plug comprising a body sized and shaped to be releasably retained in the second end of the cuff attachment. An isolator sleeve system comprising the cuff attachment and the plug.

17 Claims, 4 Drawing Sheets

(51) Int. Cl.
*B25J 21/02* (2006.01)
*G21F 7/053* (2006.01)
*A61B 42/50* (2016.01)
*A61G 10/00* (2006.01)

(56) References Cited

U.S. PATENT DOCUMENTS

| | | | |
|---|---|---|---|
| 3,811,132 | A | 5/1974 | Segonzac et al. |
| 4,010,588 | A | 3/1977 | Eisert |
| 4,089,571 | A | 5/1978 | Landy |
| 4,123,123 | A | 10/1978 | Sato et al. |
| 4,141,609 | A * | 2/1979 | Eisert ............... G21F 7/047 312/1 |
| 4,251,123 | A | 2/1981 | Brackenbush et al. |
| 5,104,206 | A | 4/1992 | Carlson et al. |
| 5,299,243 | A * | 3/1994 | Picco ............... G21F 7/053 376/287 |
| 5,662,581 | A | 9/1997 | Jennrich et al. |
| 6,715,159 | B2 | 4/2004 | Cormier |
| 8,220,675 | B2 | 7/2012 | Rohard |
| 8,328,042 | B2 | 12/2012 | Canty et al. |
| 2002/0187080 | A1 | 12/2002 | Mellor et al. |
| 2002/0189007 | A1 | 12/2002 | Cormier |
| 2008/0217366 | A1 | 9/2008 | Rohard |
| 2008/0314774 | A1 | 12/2008 | Granadino |
| 2010/0039004 | A1 | 2/2010 | Hebuterne et al. |
| 2012/0311932 | A1 | 12/2012 | Cournoyer et al. |

FOREIGN PATENT DOCUMENTS

| | | |
|---|---|---|
| EP | 0720895 B1 | 4/1995 |
| EP | 0549450 B1 | 5/1995 |
| EP | 1967335 B1 | 1/2011 |
| EP | 2767338 A2 | 8/2014 |
| EP | 2684655 B1 | 3/2015 |
| WO | 1998024599 A1 | 6/1998 |

OTHER PUBLICATIONS

English abstract of EP0720895 A1 retrieved from Espacenet on Nov. 8, 2017.
English abstract of EP1967335 A1 retrieved from Espacenet on Nov. 8, 2017.
English Abstract of EP2684655 A1 retrieved from Espacenet on Nov. 8, 2017.
Supplementary European Search Report issued in corresponding European application 1 686 943.5 dated Jul. 9, 2019.

* cited by examiner

ISOLATOR SLEEVE SYSTEMS

CROSS-REFERENCE

The present application claims convention priority to U.S. Provisional Patent Application No. 62/261,411, filed Dec. 1, 2015, entitled "ISOLATOR SLEEVE SYSTEMS" which is incorporated by reference herein in its entirety.

FIELD OF THE DISCLOSURE

The present disclosure relates to isolator sleeve systems, and more specifically although not exclusively, to isolator sleeve systems relating to a cuff portion of an isolator sleeve.

BACKGROUND OF THE DISCLOSURE

Isolators typically comprise enclosures for isolating an inside workspace from an outside environment, thus providing a barrier for contaminants entering the inside workspace and/or for contaminants leaving the workspace and causing potential harm. Examples of isolators include, but are not limited to, restricted access barrier systems (RABS), closed RABS, compounding aseptic isolators, compounding aseptic containment isolators, and gloveboxes. Isolators are useful in the pharmaceutical, medical, chemical, and electrical engineering industries, such as in the manufacture or compounding of drugs in hospitals or pharmacies, handling radioactive and other dangerous materials, and manufacturing electronic components, to name a few.

In a typical isolator system, openings such as arm ports are provided on a front face of the isolator for allowing the hands and arms of a user to access the inside workspace. Sleeves are provided which are attachable to the arm ports and which extend into the workspace. Gloves are sealingly attachable to a distal end of the sleeve typically using a sleeve cuff such as a rigid ring with annular grooves. In use, a user puts his or her arms through the arm ports and into the sleeves wearing a pair of inner disposable gloves. Once the user's arms, covered by the sleeves, are in the workspace within the isolator, the user can wipe the inner gloves with a sterilizing agent, such as isopropyl alcohol, place an outer pair of sterile gloves on the inner gloves, and attach the outer gloves to the sleeve cuff to thereby isolate the user from the inside workspace. Typically, the outer gloves are attached to the sleeve by stretching a cuff end of the outer gloves over the sleeve cuff and securing in place with a resilient ring such as a rubber 'o' ring received in one of the annular groves of the sleeve cuff.

In certain isolator uses, such as pharmaceutical compounding, regulations require frequent sterile glove changes whilst performing the compounding inside the isolator. This can be time consuming and awkward for the user and can sometimes result in tears to the new outer glove which can slow the glove change process down even further and risk contamination to the user and the isolator workspace.

The glove change process, for each hand, typically comprises removal of the resilient ring holding the outer glove to the sleeve cuff, removal of the outer glove from the user's hand, attachment of a new outer glove to the sleeve cuff and placement of the resilient ring around the new outer glove on the sleeve cuff. In some cases, the sleeve may be pulled out of the inside workspace, whilst still attached to the isolator at the port end, and the glove change performed exteriorly of the isolator. In other cases, the glove change may be performed inside the isolator workspace but the used outer glove removed through the sleeve and disposed of outside of the isolator. It will be appreciated that such glove changes of isolator systems of the prior art are awkward as single handed manipulation by the user is required and also there is a risk of breaching the inside workspace environment and subsequent contamination of the user or the outside environment by hazardous compounds.

Furthermore, inbetween work sessions at the isolator or when switching between users, a new outer glove is typically left attached to the sleeve in order to maintain the inside work environment inside the isolator. However, if the next user requires a different size of outer glove, this will necessitate a further glove change, taking up time and having the associated awkwardness and environmental breach risk mentioned above.

Therefore, there is a need for isolator sleeve systems which overcome or reduce at least some of the above-described problems.

SUMMARY OF THE DISCLOSURE

Broadly, there is provided an isolator sleeve system comprising a cuff attachment for use with an isolator sleeve cuff. The isolator sleeve system may also comprise a plug for sealing the cuff attachment, the isolator sleeve cuff and/or an isolator sleeve.

From one aspect, there is provided a cuff attachment for an isolator sleeve cuff, the cuff attachment comprising an annular band of substantially elastomeric material having an open first end and an open second end, the first end having a diameter which is wider than a diameter of the second end, the first end being adapted to be attachable to an isolator sleeve cuff and the second end being adapted to releasably retain a plug therein. The second end is preferably sized and shaped to allow a hand of a user to pass therethrough.

In certain embodiments, the second end is adapted to stretch to allow the plug to pass therethrough, in use. In certain embodiments, the second end is arranged to allow the plug to pass through the opening at the second end in both directions, i.e., in the direction of the first to second end, and in the direction of the second end to the first end. In certain embodiments, the second end is arranged to form a seal around the plug when the plug is retained in the second end, in use. The seal may be a fluid seal e.g. an air-tight seal and/or a liquid seal. In certain embodiments, the diameter of the second end is less than a diameter of the plug, when the second end is in a non-stretched state. The substantially elastomeric material of the cuff attachment may stretch to allow the plug to pass therethrough, then substantially recover once the stretching force is reduced or removed to form the seal around the plug.

In certain embodiments, the second end is adapted to stretch to allow a hand of a user to pass therethrough. In certain embodiments, the diameter of the second end is less than a diameter of the wrist of the user's hand, when the second end is in a non-stretched state. The second end may be arranged to form a seal around a wrist of the user's hand, or around any other part of the user's hand when the hand is passed through the second end from the first end. The seal may be a fluid seal e.g. an air-tight seal and/or a liquid seal. The substantially elastomeric material of the cuff attachment may stretch to allow the user's hand to pass therethrough, then substantially recover or relax when a stretching force is reduced or removed to form the seal around the user's hand or wrist.

In certain embodiments, the first end of the cuff attachment is arranged to form a seal around the isolator sleeve cuff, in use. The seal may be a fluid-tight seal, e.g. an air-tight and/or a liquid-tight seal. The first end may have a rim portion defining an opening at the first end, the opening being sized and shaped to encircle the isolator sleeve cuff when the rim portion of the first end is stretched and placed around the isolator sleeve cuff in use.

In certain embodiments, the first end may comprise a reinforced rim portion. The reinforced rim portion may define an opening at the first end. The opening may be sized and shaped to encircle or snap-fit around the isolator sleeve cuff when the reinforced rim portion of the first end is stretched and placed around the isolator sleeve cuff in use. The reinforced rim portion may comprise a thicker annular portion of the substantially elastomeric material. Alternatively, the reinforced rim portion may comprise an additional layer of material. The reinforced rim portion may require more force to stretch it compared to the force required to stretch the second end of the cuff attachment by an equivalent amount.

In certain embodiments, the diameter of the first end of the cuff attachment is less than a diameter of the isolator sleeve cuff, when the first end of the cuff attachment is in a non-stretched state. The substantially elastomeric material of the cuff attachment at the first end may stretch to allow the first end to be retained around the isolator sleeve cuff, then substantially recover or relax to form the seal around the isolator sleeve cuff when the stretching force is reduced or removed. In certain embodiments, the first end of the cuff attachment is arranged to form a snap-fit around the isolator sleeve cuff, in use. In these embodiments, additional means such as resilient rings (e.g. o-rings) or clamps for attaching the cuff attachment to the isolator sleeve cuff are not required. In use, at least a portion of the first end of the cuff attachment overlaps a portion of the isolator sleeve cuff.

In certain embodiments, the reinforced rim portion is sized and shaped to be engaged in an annular groove of the isolator sleeve cuff. The reinforced rim portion may have a width which is equal to or less than a width of the annular groove in the isolator sleeve cuff. The reinforced rim portion may have a thickness which is equal to or less than a height of the annular groove in the isolator sleeve cuff. In certain embodiments, this may assist in the retention of the cuff attachment on the isolator sleeve cuff, particularly during use. The isolator sleeve cuff may be of any suitable design and made of any suitable material. Advantageously, certain embodiments of the present cuff attachment can be retroactively attached to many types of isolator sleeve cuffs.

In certain embodiments, the substantially elastomeric material can be any material which has properties allowing stretching on application of a force and substantial or adequate recovery when the force is removed. In certain embodiments, the substantially elastomeric material is a sterilizable material. In certain embodiments, the substantially elastomeric material is a silicone, such as silicone rubber. The silicone may be a medical-use grade silicone, such as FDA approved medical use grade silicone. Alternatively, any other substantially elastomeric material may be used such as but not limited to polysiloxane, natural rubber, or other synthethic rubber.

In certain embodiments, the cuff attachment is a truncated cone shape. In certain embodiments, the first and/or second ends are circular.

In certain embodiments, the cuff attachment includes the plug and/or the isolator sleeve cuff and/or an isolator sleeve.

In certain embodiments, the plug comprises a body sized and shaped to be releasably retained in the second end of the cuff attachment. In certain embodiments, the plug comprises a body sized and shaped to be engaged with the second end of the cuff attachment. In certain embodiments, the plug comprises a body sized and shaped to enable the plug to pass through the second end when the second end is stretched.

In certain embodiments, the plug has an annular groove around the body for receiving the second end of the cuff member. The annular groove has a depth sufficient to allow retention of the second end of the cuff attachment in the annular groove. In certain embodiments, the plug has a bead or a lip against which the second end of the cuff member can abut in use.

In certain embodiments, the plug has a front face which is substantially convex. In certain embodiments, the plug has a front face which is substantially rounded. In certain embodiments, the plug has a front face which is substantially pointed. In certain embodiments, the plug has a substantially smooth surface. In certain embodiments, some or all of these features may facilitate movement of the plug through the second end of the cuff attachment. In certain embodiments, the back face of the plug body may be concave to reduce the amount of material used to make the plug.

In certain embodiments, the plug comprises a handle extending from the back face of the body. The handle is arranged to allow a user to grip the plug for pulling or pushing the plug through the second end of the cuff attachment. The handle may have a stem portion and a grip portion. The grip portion may be wider than the stem portion, and may have an indent to allow a user's thumb to rest thereon. The grip portion may have shoulders for allowing a user's fingers to rest thereon.

In certain embodiments, the annular groove may be positioned closer to the front end than the back end of the body of the plug. Alternatively, the annular groove can be positioned about mid-way from the front face to the back face. The body of the plug may have a larger diameter at the back end than the front end.

In certain embodiments, the plug may be made of any suitable material which can be sterilized, and which is more rigid than the cuff attachment. In certain embodiments, the plug is made of a polymer, such as polypropylene or polyethylene. In certain embodiments, the plug is made of a rigid polymer. In certain embodiments, the plug is of a one-piece design.

In certain embodiments, the isolator sleeve may comprise an elongate tube of material sized and shaped to accommodate the arm of a user therein. In certain embodiments, the isolator sleeve is made from a flexible material and which can provide a barrier to contaminant flow therethrough. In certain embodiments, the isolator sleeve is made from a material which can be sterilized, such as a polymer. In certain embodiments, the isolator sleeve is made from poly vinyl chloride (PVC). In certain embodiments, the isolator sleeve is free from phthalates, lead and/or metal.

In certain embodiments, the isolator sleeve cuff comprises a ring sized and shaped to be attachable to an isolator sleeve at one end, and to the cuff attachment at the other end. The isolator sleeve cuff may have a first end arranged to releasably attach to the sleeve, and a second arranged to releasably attach to the cuff attachment. In certain embodiments, the isolator sleeve cuff has an annular groove arranged to retain the first end of the cuff attachment in use. In certain embodiments, the isolator sleeve cuff is more rigid than the isolator sleeve material or the cuff attachment. In certain embodiments, the isolator sleeve cuff comprises a material which can be sterilized. In certain embodiments, the isolator sleeve cuff is made from a polymer, such as but not limited to acrylonitrile butadiene styrene.

From another aspect, there is provided an isolator sleeve system comprising a cuff attachment according to certain embodiments described above for use with an isolator sleeve or an isolator sleeve cuff, and a plug according to certain embodiments described above, and optionally an isolator sleeve and/or an isolator sleeve cuff as described above. In embodiments, where the isolator sleeve system comprises the cuff attachment and the plug, these may be used with isolator sleeves and isolator sleeve cuffs of the prior art. In certain embodiments of the isolator sleeve system, the cuff attachment and isolator sleeve may be one-piece.

From another aspect, there is provided a plug for sealing or closing an open end of a cuff attachment for an isolator sleeve cuff. In certain embodiments, the plug and/or the cuff attachment are as described above.

In use, in certain embodiments, the first end of the cuff attachment is attached to the isolator sleeve which may be extending from a wall of the isolator into a working space of the isolator; and the plug is sealingly retained in the second end of the cuff attachment, thereby sealing an environment of the working space of the isolator, which may be aseptic. Preferably, the plug is positioned with the front end of the plug pointing away from the first end of the cuff attachment, and the plug handle pointing towards the cuff attachment first end. When a user desires to access the working space inside the isolator, the user's hand is inserted into the isolator sleeve in normal fashion, and the plug handle is gripped by the user to push the plug out of the cuff attachment and into the working space of the isolator. The user's hand is passed through the second end of the cuff attachment from the sleeve to access the working space inside the isolator. The sealed environment of the working space of the isolator may be substantially maintained in certain embodiments as the second end of the cuff attachment sealingly engages with the user's hand and/or wrist as the plug is pushed out of the second end and the user's hand is pushed through the second end. In certain embodiments, the user's hand is protected by an inner glove when the hand is pushed through the second end. In certain embodiments, an outer glove may be placed on the inner glove on the user's hand. The outer glove may be a sterile glove and may be placed over the inner glove after wiping the inner glove with a sterilizing solution, such as but not limited to an alcohol such as isopropyl alcohol.

In certain embodiments, a glove change within the working space of the isolator can be effected by removing the outer glove from the hand in the isolator, discarding the removed outer glove and donning a new outer glove on the hand. In certain embodiments, this occurs while the environment of the working space remains substantially intact by virtue of the sealing engagement between the cuff attachment second end and the user's wrist and/or hand, and between the first end of the cuff attachment and the isolator sleeve cuff. Advantageously, in certain embodiments, the glove change does not require manipulation of resilient rings, such as 'o' rings, or other attachment means, to remove and attach a new outer glove. Therefore, a glove change using certain embodiments of the present cuff attachment may be faster than those of the prior art.

In certain embodiments, a retreat of the user from the isolator comprises the user holding the plug by the handle, and withdrawing his or her hand through the second end of the attachment in order to replace the sealing engagement of the second end of the cuff attachment with the user's wrist and/or hand with the sealing engagement of the second end of the cuff attachment with the plug. In certain embodiments, the plug may be sterilized before being retained in the second end such as by wiping with a sterilizing liquid such as an alcohol.

Embodiments of the presently described cuff attachment, plug, system and method, may facilitate glove changes within the isolator, and avoid glove changes between users of the same isolator especially when the users require different glove sizes. Furthermore, this arrangement may help to substantially maintain a sealed environment of the isolator during glove changes as well as between users of the isolator, and to help minimize contamination leakage into or out of the isolator.

Definitions

It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

As used herein, the term "and/or" is to be taken as specific disclosure of each of the two specified features or components with or without the other. For example "A and/or B" is to be taken as specific disclosure of each of (i) A, (ii) B and (iii) A and B, just as if each is set out individually herein.

As used herein, the term "isolator" is intended to mean any device or apparatus providing an enclosed workspace which is isolated from the outside environment exterior to the enclosure. The isolator may provide a barrier for contaminants entering the workspace e.g. for ensuring the integrity of sterile products therein, and/or a barrier for contaminants leaving the workspace e.g. for ensuring safety of at least one user outside of the isolator. Examples of isolators include, but are not limited to, restricted access barrier systems (RABS), closed RABS, barrier technology, and gloveboxes.

As used herein, the term "isolator sleeve cuff" is intended to mean a distal end (i.e. a cuff-end) of a sleeve suitable for use with an isolator. The isolator sleeve cuff may be integral with the sleeve or may be an appendage attachable to the cuff-end of the sleeve. One example of a sleeve cuff is a ring with annular grooves which can be attached to the cuff end of a sleeve at one open end and can be attached to a glove at the other open end.

BRIEF DESCRIPTION OF DRAWINGS

Further aspects and advantages of the present invention will become better understood with reference to the description in association with the following in which.

DETAILED DESCRIPTION

The present disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the following description, the same numerical references refer to similar elements.

Broadly, there is provided a cuff attachment 10 arranged to sealingly engage at one end with an isolator sleeve cuff; and at the other end either with a user's hand and/or wrist during the user working in the isolator, or a plug when there is no user work being performed in the isolator.

Figure 1:
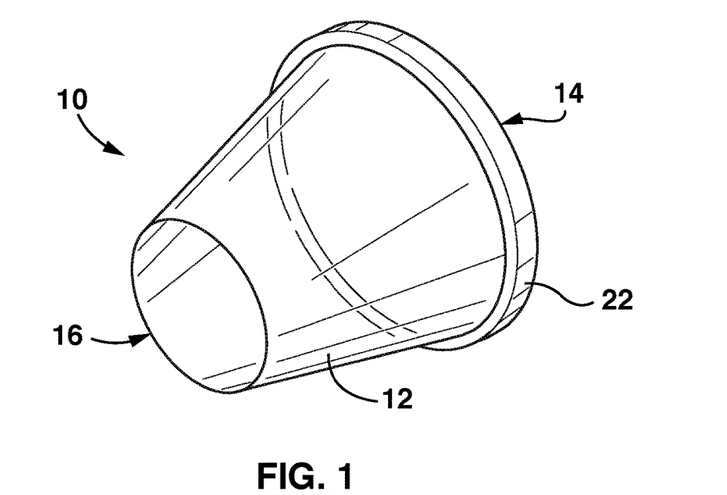
FIG. 1 illustrates a perspective view of one embodiment of a cuff attachment of the present disclosure.

Referring to FIG. 1, there is illustrated one embodiment of the cuff attachment 10 of the present disclosure. The cuff attachment 10 comprises an annular band 12 of substantially elastomeric material having a truncated cone shape with a first end 14 and a second end 16, the first and second ends 14, 16 being open and substantially circular, and the diameter of the first end 14 being larger than a diameter of the second end 16. The cuff attachment is sheath-like and flexible. As can best be seen in FIG. 4, the first end 14 of the cuff attachment 10 is arranged to be detachably attachable to an isolator sleeve cuff 18. As best seen in FIG. 3, the second end 16 of the cuff attachment 10 is arranged to releasably retain a plug therein, such as the plug 20 shown in FIGS. 2a, 2b and 3. In this embodiment, the substantially elastomeric material of the cuff attachment 10 is silicone rubber, such as FDA approved medical-grade silicone rubber, although any other suitable substantially elastomeric material may be used.

Figure 4:
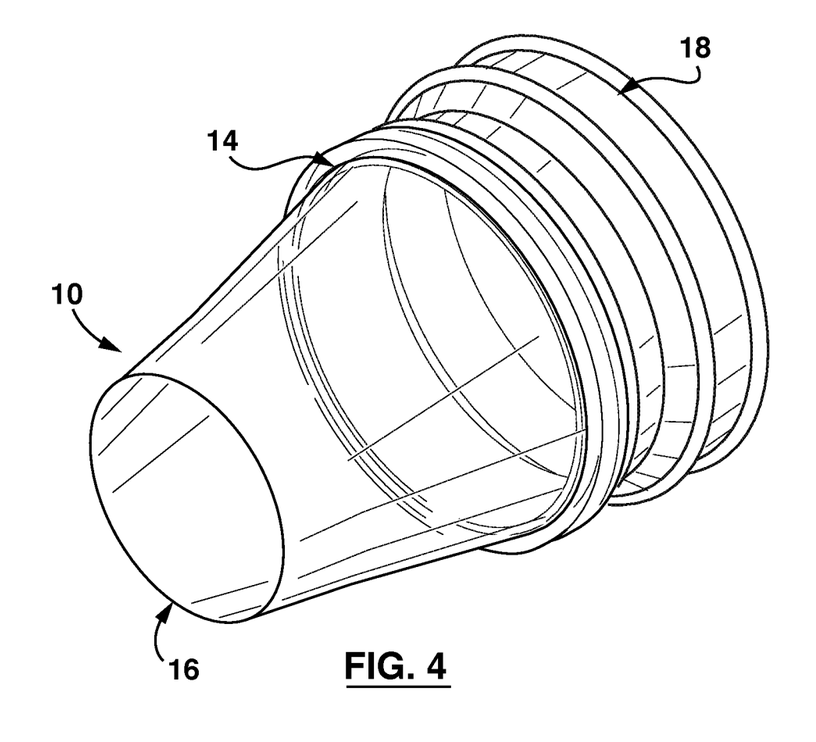
FIG. 4 illustrates the cuff attachment of FIG. 1 attached to a sleeve cuff, in use, according to one embodiment of a system of the present disclosure.

The first end 14 of the cuff attachment 10 is arranged to sealingly engage with the isolator sleeve cuff 18 to form a seal with the isolator sleeve cuff, when attached in use. In this embodiment, the first end 14 has a diameter less than a diameter of the isolator sleeve cuff 18, when the first end 14 is in a non-stretched state. The cuff attachment 10 is arranged to stretch when a force is applied so that the first end 14 can be stretched over the isolator sleeve cuff 18, and once the force is removed, the cuff attachment 10 at least partially recovers towards its unstretched state to form a snap-fit around the isolator sleeve cuff 18. The cuff attachment 10 can be removed from the isolator sleeve cuff 18 by stretching the first end 14 away from the isolator sleeve cuff 18.

Figure 5A:
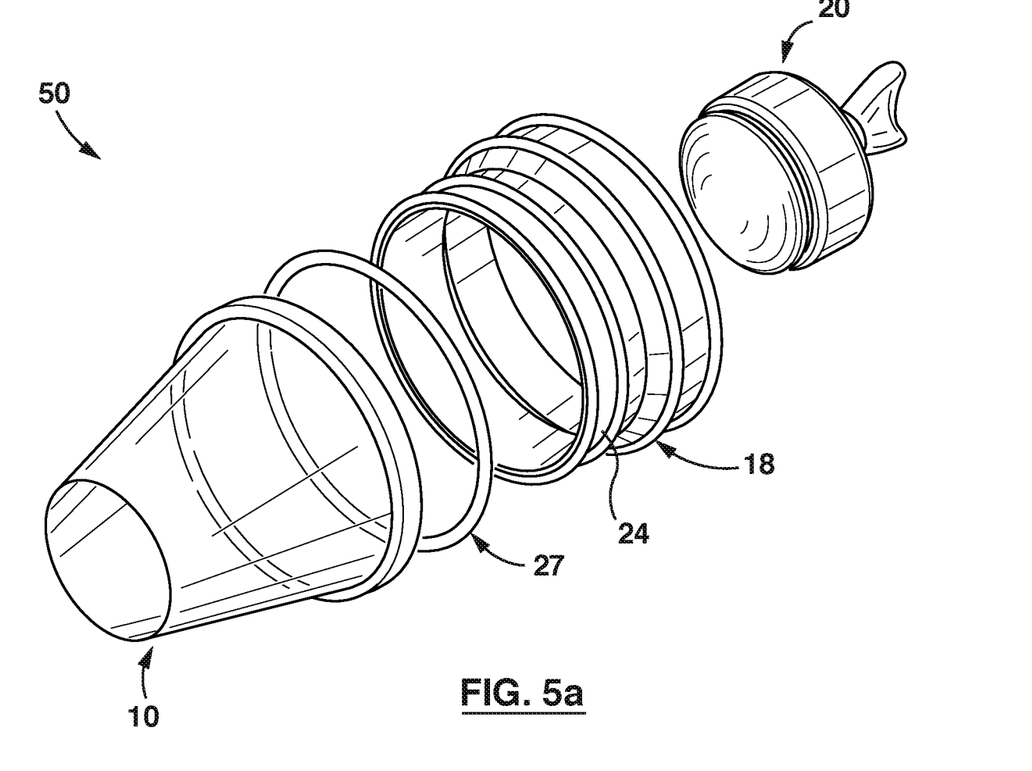
FIGS. 5a and 5b illustrate an expanded and collapsed view, respectively, of the cuff attachment of FIG. 1, the plug of FIG. 2, the sleeve cuff of FIG. 3, and an o-ring according to one embodiment of a system of the present disclosure.

The first end 14 of the cuff attachment 10 has a reinforced rim portion 22 which is sized and shaped to engage with an annular groove 24 on an outer surface of the isolator sleeve cuff 18 (FIG. 5a). Specifically, as seen best in FIG. 4, the reinforced rim portion 22 has a width which is narrower than a width of the annular groove 24 so that the reinforced rim portion 22 is received within the annular groove 24. The reinforced rim portion 22 comprises a thicker annular portion of the substantially elastomeric material. Alternatively, the reinforced rim portion may comprise an additional layer(s) of other material, or may comprise a rolled up or otherwise multi-layered portion of the annular band to form the thicker annular portion. Alternatively, the reinforced rim portion may comprise any other configuration which increases the amount of force required to stretch the first end compared to a non-reinforced portion of the annular body. The reinforced rim portion 22 may help retention of the first end 14 of the cuff attachment 10 on the isolator sleeve cuff 18, during use, without necessitating the use of securing devices to secure the cuff attachment 10 to the isolator sleeve cuff 18, such as o-rings and clamps. In other embodiments (not shown), instead of or in addition to the reinforced rim portion, there may be provided securing devices such as o-rings 27 and/or clamps, or any other means of securing the cuff attachment 10 to the isolator sleeve cuff 18.

Figure 6A:
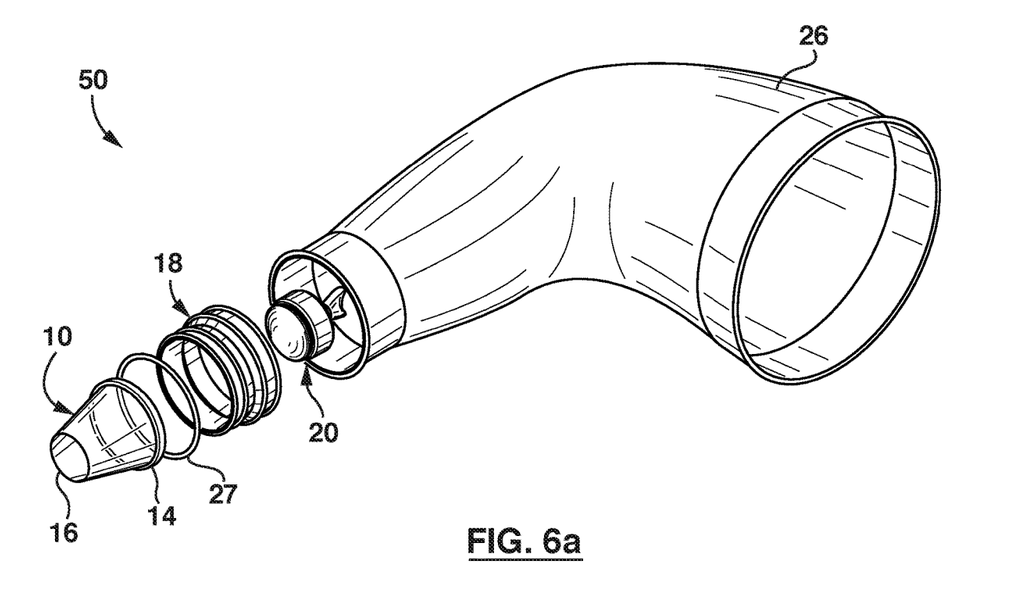
FIGS. 6a and 6b illustrate an expanded and collapsed view, respectively, of the system of FIGS. 5a and 5b and an isolator sleeve, according to one embodiment of a system of the present disclosure.
Figure 6B:
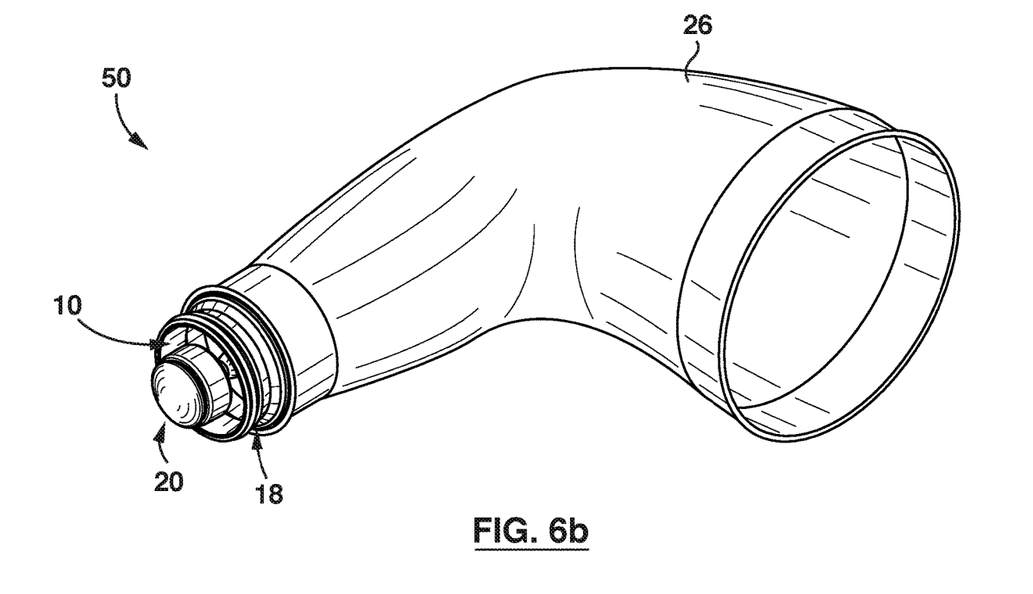

Turning now to FIGS. 6a and 6b, the isolator sleeve cuff 18 is also arranged to sealingly engage with an isolator sleeve 26 (FIGS. 6a and 6b). The attachment of the isolator sleeve cuff 18 to the isolator sleeve 26 may be in any manner and using any suitable fastening mechanism. For example, the isolator sleeve cuff 18 may include windings on an inner surface (not shown) for engagement with windings on a distal end of the sleeve 26 (not shown). Alternatively, a resilient ring such as an 'o' ring (not shown) may be used over the isolator sleeve 26 positioned on the isolator sleeve cuff 18. Alternatively, clamps or other attachment means may be used to secure the sleeve 26 to the sleeve cuff 18. In this embodiment, the isolator sleeve cuff 18 is made of a rigid material such as a polymer e.g. acrylonitrile butadiene styrene, although any other suitable material may be used.

Figure 5B:
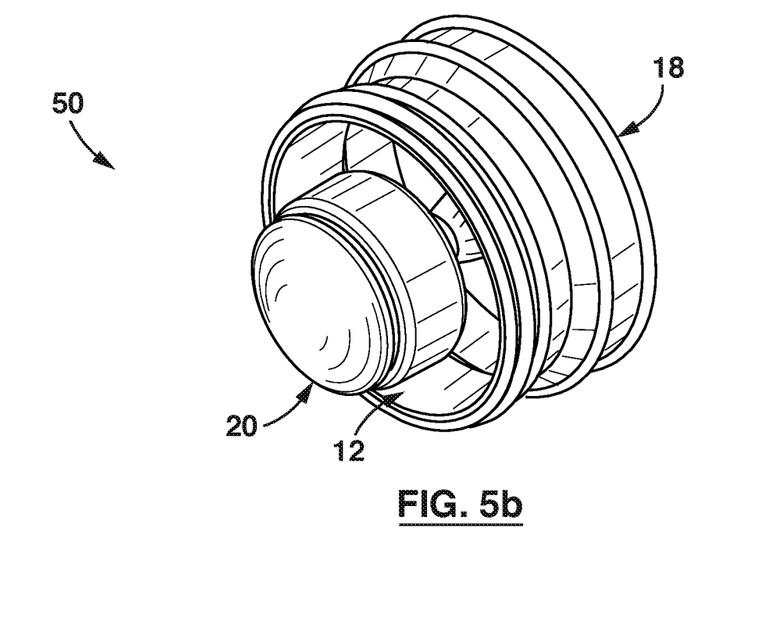

It will be appreciated that use of the cuff attachment 10 is not limited to the isolator sleeve cuff 18 illustrated in FIGS. 4-6 but can be used, such as retroactively, with any suitable isolator sleeve cuff. For example, instead of an annular groove, the cuff attachment may include an annular bead or lip on its outer surface for engagement with the cuff attachment 10. In other embodiments, the isolator sleeve cuff may be integral with an isolator sleeve.

Turning now to the second end 16 of the cuff attachment 10, the second end 16 is configured to retain the plug 20 in sealing engagement, such as when it is desired to seal the second end 16 in use. The second end 16 is also configured to allow the plug 20 to pass therethrough, when a force is applied in use. The second end 16 is also configured to allow a hand of a user (not shown) to pass therethrough, when a force is applied, yet to form a seal around a wrist of the user's hand, when the hand is retained in the second end 16. In this respect, a diameter of the second end 16 is less than a diameter of the plug 20 and a diameter of a user's wrist, when the second end is in a non-stretched state.

Figure 2A:
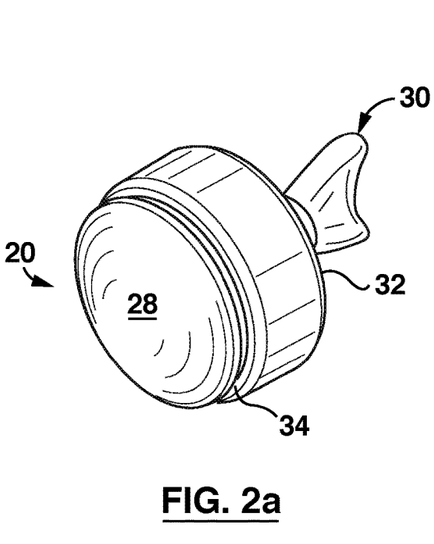
FIGS. 2a and 2b illustrate a perspective view and a side view, respectively, of one embodiment of a plug of the present disclosure.
Figure 2B:
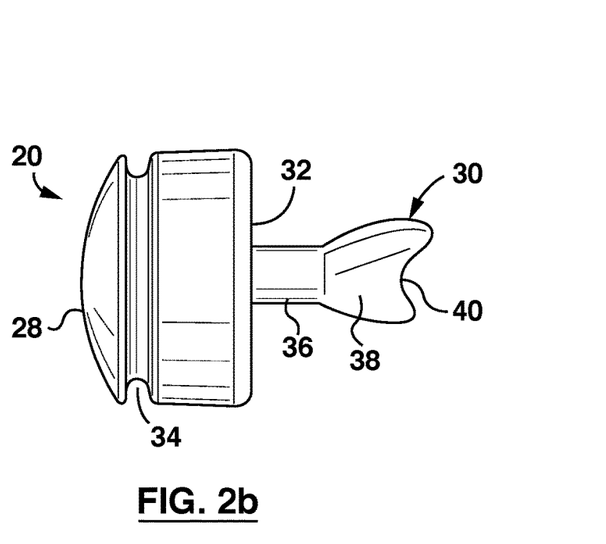
Figure 3:
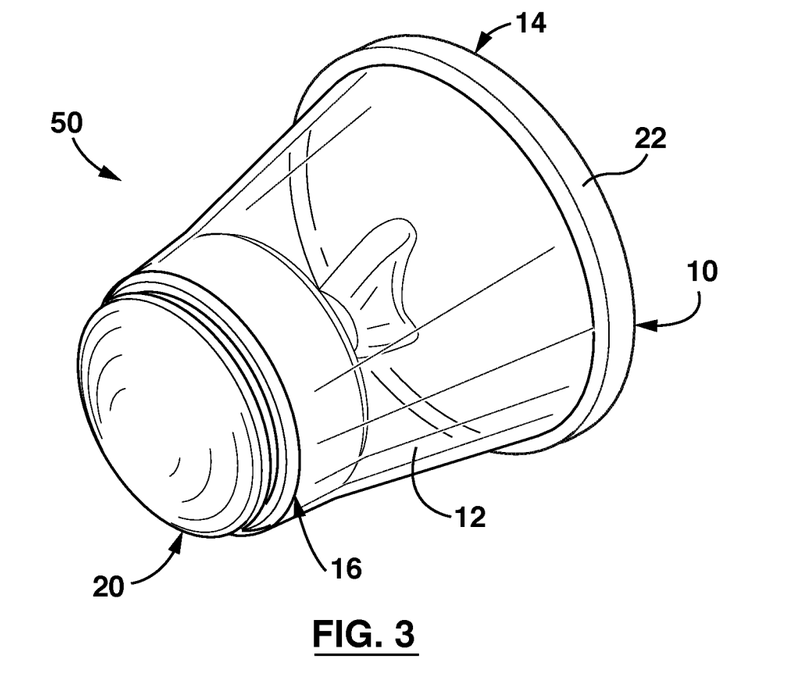
FIG. 3 illustrates the plug of FIGS. 2a and 2b attached to the cuff attachment of FIG. 1, in use, according to one embodiment of a system of the present disclosure.

Turning now to the plug 20 with reference to FIGS. 2a and 2b, it can be seen that the plug 20 comprises a body sized and shaped to be releasably retained in the second end 16 of the cuff attachment 10, as well as to be able to pass through the second end 16 when a force is applied. More specifically, the plug 20 has a front face 28 at a front end which is substantially convex or rounded and a handle 30 extending from a back face 32 at a back end of the body. The back end of the plug body is concave (not shown) to reduce the amount of material used to make the plug 20. In certain embodiments, the body of the plug 20 has a substantially smooth surface and a slightly larger diameter at the back end than at the front end which may help to push the plug through the second end 14 of the cuff attachment 10. The plug 20 has an annular groove 34 around the body in which the second end 14 of the cuff attachment 10 is received during retention of the plug 10 in the second end 14. In certain embodiments, the annular groove 34 may be positioned closer to the front end than the back end of the body of the plug 20. Alternatively, the annular groove 34 can be positioned about mid-way from the front face to the back face.

The handle 30 is arranged to allow a user to grip the plug 20 for pulling or pushing the plug 20 through the second end 14 of the cuff attachment 10. The handle 30 has a stem portion 36 and a grip portion 38, the grip portion 38 being wider than the stem portion 36, and having an indent 40 to allow a user's thumb to rest thereon. The grip portion 38 has shoulders for allowing a user's fingers to rest thereon.

The plug 20 is made of any suitable material which can be sterilized, and which is more rigid than the cuff attachment 10. In this embodiment, the plug 20 is made of polypropylene and is of a one-piece design. However, the plug may be made of any other polymer and/or may have a multi component design.

Turning now to the isolator sleeve 26 (FIG. 6), in this embodiment the isolator sleeve 26 comprises an elongate tube of material sized and shaped to accommodate the arm of a user therein. The isolator sleeve 26 is made from a flexible material and which can provide a barrier to contaminant flow therethrough, such as poly vinyl chloride (PVC), or any other suitable material. The isolator sleeve is free from phthalates, lead and/or metal in this embodiment.

In use, the first end 14 of the cuff attachment 10 is attached to the isolator sleeve 26 which is attached to the isolator (not shown); and the plug 20 is sealingly retained in the second end 16 of the cuff attachment 10, thereby sealing an environment of the working space of the isolator, which may be aseptic. The plug 20 is positioned with the front end of the plug 20 pointing away from the first end 14 of the cuff attachment 10, and the plug handle 30 pointing towards the cuff attachment first end 14. When a user desires to access the working space inside the isolator, the user's hand is inserted into the isolator sleeve 26 in normal fashion, and the plug handle 30 is gripped by the user to push the plug 20 out of the cuff attachment 10 and into the working space of the isolator. The user's hand is passed through the second end 14 of the cuff attachment 10 from the sleeve 26 to access the working space inside the isolator. The sealed environment of the working space of the isolator may be substantially maintained in certain embodiments as the second end 14 of the cuff attachment 10 sealingly engages with the user's hand and/or wrist as the hand is pushed through the second end 14. The user's hand is protected by an inner glove when the hand is pushed through the second end 14, and an outer glove is placed over the inner glove after the hand has been pushed through the cuff attachment 10 and the inner glove cleaned with a sterilizing solution such as an alcohol.

In pharmacy compounding, particularly for chemotherapy drugs for example, outer gloves (i.e. the gloves that come into contact with the drug) must be changed every 30 minutes for protection of the user in case of drug penetration through the gloves. In this embodiment, an outer glove is changed within the working space of the isolator by removing the outer glove from the hand in the isolator, discarding the removed outer glove and placing a new outer glove on the inner glove. In certain embodiments, this occurs while the environment of the working space remains substantially intact by virtue of the sealing engagement between the cuff attachment 10 second end 16 and the user's wrist and/or hand, and between the first end 14 of the cuff attachment 10 and the isolator sleeve cuff 18. Advantageously, in certain embodiments, the glove change does not require manipulation of resilient rings, such as 'o' rings, or other attachment means, to remove and attach a new outer glove. Therefore, a glove change using certain embodiments of the present cuff attachment may be faster than those of the prior art.

A retreat of the user from the isolator, for example to allow another user to work in the isolator, comprises the user holding the plug 20 by the handle 30, and withdrawing his or her hand through the second end 16 of the cuff attachment 10 in order to replace the sealing engagement of the second end 16 of the cuff attachment 10 with the user's wrist and/or hand with the sealing engagement of the second end 16 of the cuff attachment 10 with the plug 20. The plug is preferably wiped with a sterilizing liquid such as alcohol before being retained in the cuff attachment 10. In this way, the isolator environment may be maintained whilst the isolator is not in use. Also when a new user comes to the isolator, he or she inserts their arm in through the isolator sleeve and replaces the plug with their hand and/or wrist and starts work in the isolator after donning a pair of new and clean outer gloves. An outer glove change is not necessary.

There is also provided an isolator sleeve system 50, which according to the embodiment of FIG. 3, comprises the cuff attachment 10 and the plug 20.

The isolator sleeve system 50 of FIGS. 5*a* and 5*b* differs from that of FIG. 3, in that the isolator sleeve system 50 additionally includes the isolator sleeve cuff 18.

The isolator sleeve system of FIGS. 6*a* and 6*b* differs from that of 5*a* and 5*b* in that the isolator sleeve system 50 additionally includes the isolator sleeve 26.

Further embodiments of the isolator sleeve system 50 may comprise any of the systems of FIGS. 3, 5*a* and 5*b*, or 6*a* and 6*b* together with an isolator (not shown).

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein.

It should be appreciated that the invention is not limited to the particular embodiments described and illustrated herein but includes all modifications and variations falling within the scope of the invention as defined in the appended claims.

The invention claimed is:

1. A cuff attachment for an isolator sleeve cuff, the cuff attachment comprising an annular band of substantially elastomeric material having an open first end, an open second end, and a plug for sealing the second end, the first end having a diameter which is wider than a diameter of the second end, the first end being adapted to be attachable to an isolator sleeve cuff, and the second end being adapted to releasably retain the plug therein, the diameter of the second end being less than a diameter of the plug when the second end is in a non-stretched state, and the second end being adapted to stretch to allow the plug to pass therethrough, and to substantially recover to form a seal around the plug when the plug is retained in the second end, in use; and the plug comprising a body sized and shaped to be releasably retained in the second end of the cuff attachment, and to be able to pass through the second end when the second end is stretched.

2. The cuff attachment of claim 1, wherein the second end is arranged to form a seal around a wrist of the user's hand, when the hand is passed through the second end from the first end.

3. The cuff attachment of claim 2, wherein the diameter of the second end is less than a diameter of the wrist of the user's hand, when the second end is in the non-stretched state.

4. The cuff attachment of claim 1, wherein the first end is configured to be detachably attachable to the isolator sleeve cuff.

5. The cuff attachment of claim 1, wherein the first end is arranged to form a seal around the isolator sleeve cuff, in use.

6. The cuff attachment of claim 1, wherein the first end comprises a reinforced rim portion.

7. The cuff attachment of claim 6, wherein the reinforced rim portion comprises a thicker annular portion of the substantially elastomeric material.

8. The cuff attachment of claim 6, wherein the reinforced rim portion is sized and shaped to be engaged in an annular groove of the isolator sleeve cuff.

9. The cuff attachment of claim 1, wherein the diameter of the first end is less than a diameter of the isolator sleeve cuff, when the first end is in the non-stretched state.

10. The cuff attachment of claim 1, wherein the cuff attachment is a truncated cone shape.

11. The cuff attachment of claim 1, wherein the plug comprises a handle extending from a back face of the body.

12. The cuff attachment of claim 1, wherein the plug has an annular groove around the body for receiving the second end of the cuff attachment.

13. The cuff attachment of claim 1, wherein the plug has a front face which is substantially convex.

14. The cuff attachment of claim 1, wherein the body of the plug has a larger diameter at a back end than a front end.

15. The cuff attachment of claim 1, further comprising an isolator sleeve having the isolator sleeve cuff, the isolator sleeve cuff having a first end arranged to releasably attach to a sleeve, and a second end arranged to releasably attach to the cuff attachment.

16. The cuff attachment of claim 1, wherein the isolator sleeve cuff has an annular groove arranged to retain the first end or a reinforced rim portion of the first end of the cuff attachment in use.

17. The cuff attachment of claim 1, wherein the open second end is arranged to allow the plug to pass therethrough in a direction of the first end to the second end, and in a direction of the second end to the first end.

* * * * *